(12) United States Patent
Heilala et al.

(10) Patent No.: US 8,491,599 B2
(45) Date of Patent: Jul. 23, 2013

(54) APPARATUS AND METHOD FOR AIMING A SURGICAL TOOL

(75) Inventors: Matt A. Heilala, Anchorage, AK (US);
Avery B. Munoz, Eagle River, AK (US);
John S. Steinberg, Oak Hill, VA (US);
Glenn Weinraub, Danville, CA (US)

(73) Assignee: Lower Extremity Innovations, LLC, Anchorage, AK (US)

( * ) Notice: Subject to any disclaimer, the term of this patent is extended or adjusted under 35 U.S.C. 154(b) by 404 days.

(21) Appl. No.: 12/641,342

(22) Filed: Dec. 18, 2009

(65) Prior Publication Data
US 2010/0160925 A1 Jun. 24, 2010

Related U.S. Application Data

(60) Provisional application No. 61/203,245, filed on Dec. 19, 2008.

(51) Int. Cl.
*A61B 17/58* (2006.01)
*A61B 17/60* (2006.01)
*A61F 2/00* (2006.01)

(52) U.S. Cl.
USPC .......................................................... 606/99

(58) Field of Classification Search
USPC .......... 606/55–58, 96–98, 102–104, 86 R–89
See application file for complete search history.

(56) References Cited

U.S. PATENT DOCUMENTS

| | | | |
|---|---|---|---|
| 4,722,331 A * | 2/1988 | Fox | 606/96 |
| 5,116,344 A | 5/1992 | Sundqvist | |
| 5,688,284 A | 11/1997 | Chervitz et al. | |
| 6,520,969 B2 | 2/2003 | Lambrecht et al. | |
| 6,542,770 B2 | 4/2003 | Zylka et al. | |
| 6,955,284 B2 | 10/2005 | Zakel et al. | |
| 2005/0216026 A1 | 9/2005 | Culbert | |
| 2006/0069394 A1 | 3/2006 | Weiler et al. | |
| 2007/0270877 A1 | 11/2007 | Park | |

FOREIGN PATENT DOCUMENTS

| | | |
|---|---|---|
| FR | EP0428452 A1 | 5/1991 |
| WO | 2008106593 A2 | 4/2008 |

* cited by examiner

*Primary Examiner* — Andrew Yang
*Assistant Examiner* — Diana S Jones
(74) *Attorney, Agent, or Firm* — Herbert A. Newborn

(57) ABSTRACT

An easy to use mechanical apparatus intended for aiming a surgical tool is provided. Embodiments of the apparatus offer movement in multiple planes while guaranteeing, given proper placement of the leading end of a locator tool at a target, that the leading end of a second tool be placed at precisely the same target. Methods of using the apparatus as well as kits including the apparatus are also provided.

40 Claims, 6 Drawing Sheets

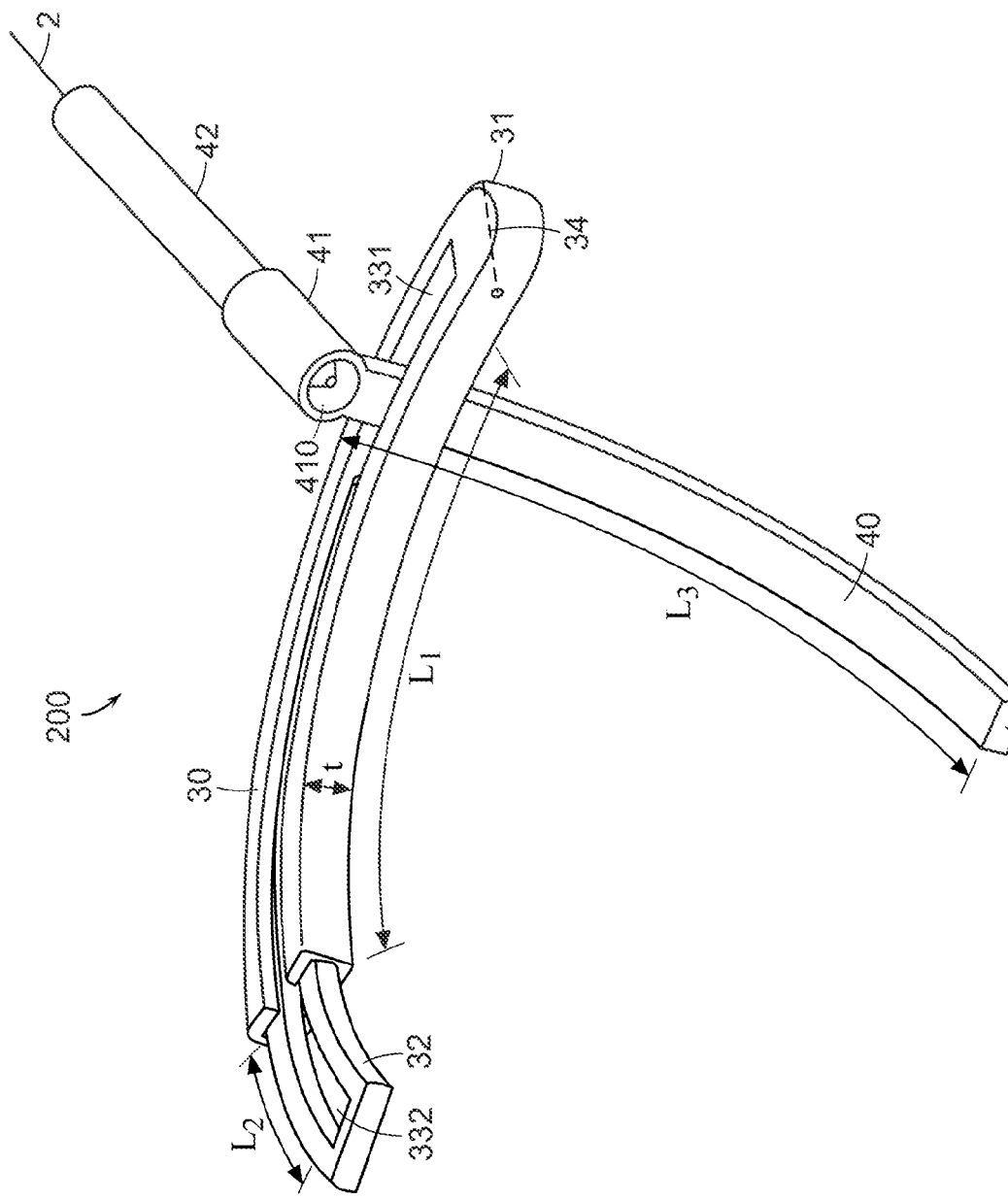
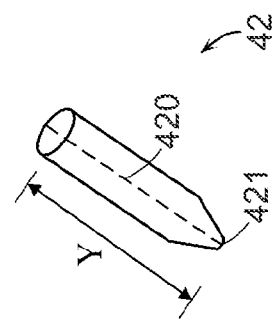
FIG. 2(a)
FIG. 2(b)

APPARATUS AND METHOD FOR AIMING A SURGICAL TOOL

CROSS-REFERENCE TO RELATING APPLICATION(S)

This application claims the benefit of U.S. Provisional Patent Application Ser. No. 61/203,245, filed Dec. 19, 2008 which is incorporated herein by reference.

TECHNICAL FIELD

The present invention relates to devices and procedures to facilitate accurate placement of hardware. More particularly, accurate positioning of surgical tools is assured through use of the methods and apparatus disclosed.

BACKGROUND ART

The effectiveness of most surgical procedures depends in large part on the accuracy with which hardware is introduced. Guide pin and drill guides are very useful in achieving improved accuracy of hardware placement.

Many current guide or aiming models offer very limited range of motion. Many are specifically designed for situations in which a target point is positioned within a more discernible intra-articular space rather than within a bone or other anatomical structure. For many procedures, surgeons must rely on cumbersome C-arm fluoroscopy in the operating room to confirm the location of hardware. This, and other forms of intra-operative x-ray imaging, inevitably leads to excessive radiation exposure as well as increased operating times. There is a need for a single, easy to use, mechanical apparatus that offers movement in multiple planes while guaranteeing, given proper placement of the leading end of a first surgical tool (sometimes described herein as a locator tool) at a target (perhaps not discernibly located within a bone or within a joint), that the leading end of a second surgical tool be placed at precisely the same target.

SUMMARY OF THE INVENTION

Embodiments of the present invention address the need for an easy to use, mechanical apparatus that offers movement in multiple planes while guaranteeing, given proper placement of the leading end of a locator tool at a target (perhaps not discernibly located within a bone or within a joint), that the leading end of a second surgical tool be placed at precisely the same target. A surgical guide for aiming at least one tool toward a surgical target is provided in a first embodiment. The guide has a guide reference plane. The surgical guide has a base and at least one member that engages with the base. The base has a base thickness. A track is cut through the base thickness; the at least one member sized to be receivable in the track to engage with the base. The track has a constant track curvature so as to define a base arc of a base circle. The base circle is spatially oriented in the guide reference plane. Further, the base has a base channel oriented upon a radius of the base circle. The base channel is sized and shaped so as to be capable of accepting a locator tool therethrough. The at least one member has a constant member curvature equal to the constant track curvature of the base so as to define a member arc of a member circle; the member circle is spatially oriented in a member arc plane. When engaged with the base, the base circle and the member circle define a sphere having a sphere center located at the surgical target. Further, the at least one member has a member channel sized and shaped so as to be capable of accepting the at least one tool therethrough; the member channel is oriented upon a radius of the member circle, such that when the at least one member is engaged with the base, both the base channel and the member channel are aligned toward the surgical target. The member arc plane may be oriented orthogonal to the guide reference plane.

In further embodiments, the base may have an adjustable base arc length. The base may have first and second base portions. The first base portion may have a first base arc length with a base portion orifice extending along the first base arc length. The second base portion is sized to be insertable into the base portion orifice to slidingly engage with the first base portion. The second base portion has a second base arc length. When the first and second base portions are engaged, the adjustable base arc length is measurable by adding the first base arc length to an adjustable fraction of the second base arc length. An embodiment may also feature a base locking mechanism to rigidly secure the first and second base portions together at a chosen adjustable base arc length. The at least one member may have an adjustable member arc length. The at least one member may have first and second member portions. The first member portion may have a first member arc length with a member portion orifice extending along the first member arc length. The second member portion is sized to be insertable into the member portion orifice to slidingly engage with the first member portion. The second member portion has a second member arc length, such that when the first and second member portions are engaged, the adjustable member arc length is measurable by adding the first member arc length to an adjustable fraction of the second member arc length. An embodiment may also feature a member locking mechanism to rigidly secure the first and second member portions together at a chosen adjustable member arc length. Further embodiments for which both the base and the at least one member have adjustable arc lengths and may also have respective locking mechanisms are also provided.

In another embodiment, a surgical guide for aiming at least one tool toward a surgical target is provided. The guide has a guide reference plane. The surgical guide has a base and at least one member that engages with the base. The base has a base thickness, a base width disposed within the reference plane and a track cut through the base thickness. The track has a uniform track width. The track has a constant track curvature so as to define a base arc of a base circle. The base circle is oriented within the reference plane. Further, the base has a base channel cut through the base width; the base channel is disposed within the reference plane; the base channel is sized and shaped so as to be capable of accepting a locator tool therethrough. The at least one member is sized so as to be receivable in the track to engage with the base. The at least one member has a constant member curvature equal to the constant track curvature so as to define a member arc of a member circle. When engaged with the base, the member arc is disposed within a member arc plane that is oriented orthogonal to the reference plane. When the at least one member and the base are engaged, the base circle and the member circle define a sphere having a sphere center located at the surgical target. The at least one member has a member channel is cut through the member; the member channel is disposed within the member arc plane; the member channel is sized and shaped so as to be capable of accepting the at least one tool therethrough. As a result, when the at least one member is engaged with the base, both the base channel and the member channel are aligned toward the surgical target.

In yet other embodiments, the base may have an adjustable base arc length. The base may have first and second base portions. The first base portion may have a first base arc length with a base portion orifice extending along the first base arc length. The second base portion is sized to be insertable into the base portion orifice to slidingly engage with the first base portion. The second base portion has a second base arc length. When the first and second base portions are engaged, the adjustable base arc length is measurable by adding the first base arc length to an adjustable fraction of the second base arc length. An embodiment may also feature a base locking mechanism to rigidly secure the first and second base portions together at a chosen adjustable base arc length.

In additional guide embodiments, the at least one member (and/or the base) may have a channeled tool support member (and/or base) extender section. Channels of the extender section(s) is/are aligned with the member channel and/or the base channel. The member (and/or base) extender section has an extender section length, this length is slidingly adjustable along a radius of the member (and/or base) circle respectively.

Methods for aiming at least one tool toward a surgical target are also provided. A first step is to define a surgical target as a position of a proximal end of a locator tool (the locator tool also has a distal end). An embodiment of the surgical guide is then provided. Its base is engaged with the locator tool by passing the distal end of the locator tool through the base channel. The at least one member of the surgical guide is engaged with the base of the surgical guide. Subsequently, the at least one tool is passed through the member channel. The at least one tool will necessarily be aimed at the surgical target.

Methods for adjusting the base arc length of embodiments of the surgical guide are provided. A second portion of a base or a member may slide within the first portion of a base or member to a chosen (extended) arc length. A next step may be engaging a base or member locking mechanism for rigidly securing the second base or member portion within the first base or member portion at a chosen arc length.

A method for selectively orienting the at least one tool within the base of the surgical guide is provided. A first step is to slide the at least one member essentially within the guide reference plane and along an arc length of the track disposed within the base of an embodiment of the surgical guide. The at least one member is then slid along an arc length of the member. The at least one member is then positioned within the base of the surgical guide at the selected orientation.

In further embodiments, a surgical guide kit is provided. The kit contains any of the surgical guide embodiments and an electrical circuit capable of being coupled with the locator tool at one terminus and capable of being coupled with the at least one tool at a second terminus. The kit may also have a sensor in electrical communication with the electrical circuit; the sensor activatable only upon completion of the electrical circuit to indicate that the at least one tool has its proximal end located at the target in electrical communication with the proximal end of the locator tool.

BRIEF DESCRIPTION OF THE DRAWINGS

FIG. 2(a) shows a surgical guide in accordance with an embodiment; FIG. 2(b) illustrates a tool holder used in conjunction with the embodiment of FIG. 2(a);

DETAILED DESCRIPTION OF SPECIFIC EMBODIMENTS

Figure 1A:
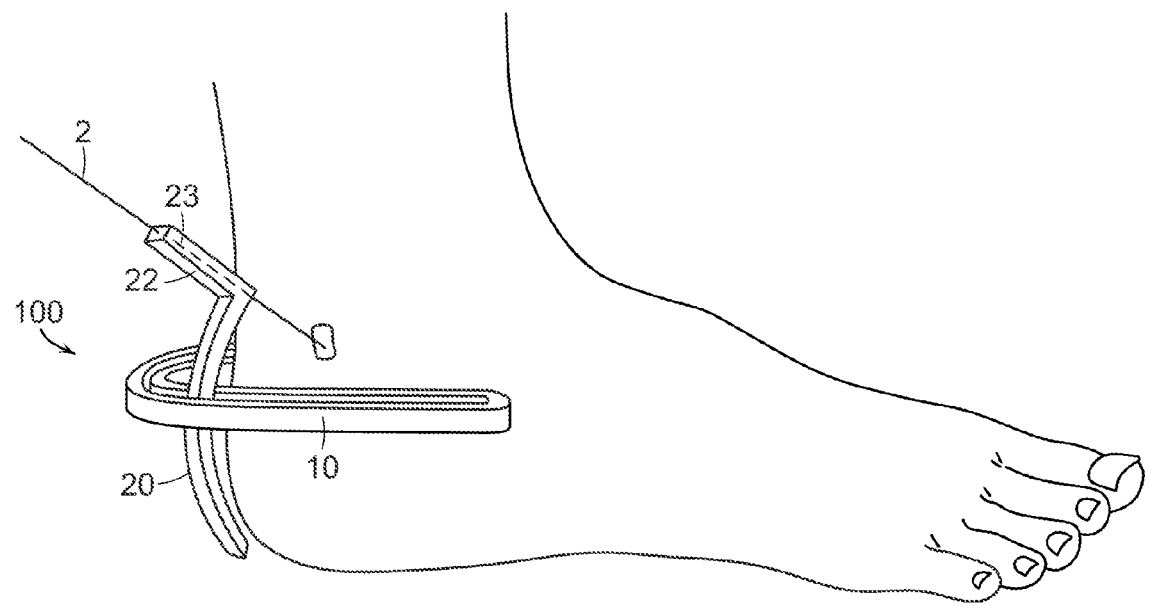
FIGS. 1(a) and (b) illustrate the use of a surgical guide embodiment in foot surgery.
Figure 1B:
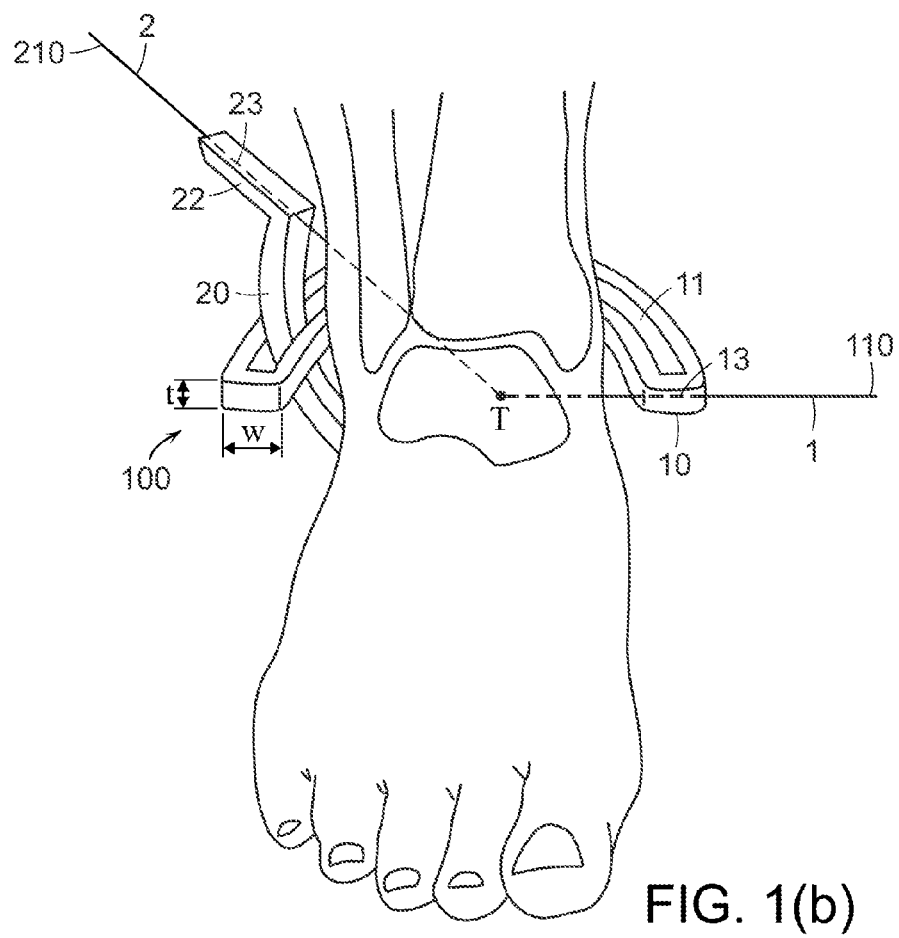

FIGS. 1(a) and 1(b) show a surgical site, in particular, that of a human foot and selected associated bones. Locator tool 1 has been drilled (or otherwise inserted) into the foot. The proximal end of locator tool 1 is lodged within bone at surgical target T. The surgeon wishes to install tool 2 such that its proximal end will also reside at surgical target T. The surgeon wishes to insure the accuracy of this placement without the use of ancillary equipment such as intra-operative x-ray imaging devices to accurately locate surgical target T.

Accurate placement of tool 2 is facilitated by the use of surgical guide 100. The embodiment of surgical guide 100 illustrated in FIGS. 1(a) and 1(b) has base 10 and member 20. Base 10 has track 11 cut through base thickness t. Track 11 is shown as having a uniform track width; track 11 also has a constant curvature defining an arc of a base circle. Base 10 also has base channel 13 cut through base width W. Base channel 13 is sized to accept locator tool 1. In operation, locator tool 1 will be placed before introducing surgical guide 100. Base 10 may then be put into use by first inserting distal end 110 of locator tool 1 into base channel 13. Locator tool 1 may be marked (e.g. laser mark, groove, notch or similar) to identify proper positioning of base 10 with respect to surgical target T such that track 11 is uniformly offset from surgical target T. Once base 10 is appropriately placed, the curvature of track 11 will define a base arc of a base circle which will have surgical target T at its center. Member 20 is sized so as to be receivable through track 11 at any position around the base arc. Member 20 has the same constant curvature as track 11, thereby defining an arc of a member circle orthogonal to the base circle, in turn, defining a sphere whose center should accurately coincide with surgical target T. In the present embodiment, member 20 features a channeled tool support member extender section 22. Channel 23 is aligned with and extends along extender section 22. Once the surgeon establishes a desirable position around the base arc length (formed by track 11) for member 20 to be located, tool 2 is inserted through channel 23 and remains handleable at its distal end 210. Tool 2 may be marked (e.g. laser mark, groove, notch or similar) along its length to indicate proper insertion depth. The surgeon may then force or drill tool 2 and be assured of accurately moving the proximal end of tool 2 to surgical target T. Surgical guide 100 is to be made of rigid material capable of maintaining its shape and curvature given the force required to install tool 2 into bone or other structures.

FIG. 2(a) illustrates another surgical guide embodiment. Surgical guide 200 has base 30 and member 40. Base 30 has first base portion 31 and second base portion 32. First base portion 31 has a base portion orifice extending along its length and has track 331 cut through first base portion thickness t. Track 331 has a uniform track width and also has a constant curvature defining an arc of a base circle of arc length $L_1$. Second base portion 32 has track 332 (having the same uniform track width and constant curvature as track 331) cut through its thickness (which is of somewhat lesser thickness dimension than first base portion thickness t so as to be receivable within the base portion orifice of first base portion 31). As a result, second base portion 32 is slidingly engageable with first base portion 31. As shown in FIG. 2(a), much of second base portion 32 remains within the base portion orifice. A telescopic effect is created so that a variable arc length of base 30 may be chosen to be equal to or greater than $L_1$. To facilitate compact storage of base 30 when the guide 200 is not in use or to facilitate initial engagement of base 30 with a locator tool 1 (not shown) through base channel 34 in a surgical procedure area of limited space/accessibility, second base portion 32 may beneficially totally reside within the base portion orifice of first base portion 31. In FIG. 2(a), most of second base portion 32, is shown to reside within the base portion orifice of first base portion 31, adding an operator-adjustable effective arc length $L_2$ of track 332 to arc length $L_1$ of track 331.

In the present embodiment, member 40 has a fixed length $L_3$. The cross-section of edge 44, as well as that of the entire length $L_3$ are sized to be acceptable into and to slidingly engage with track 331 (or, equivalently, track 332) to provide both height and angular variation to the entry of tool 2 as tool 2 is to be directed toward surgical target T (not shown) along a radius of a selectable member circle, the member circle oriented orthogonally to the base circle. Member 40 also has extender section 41. Extender section 41 has member channel 410 disposed within it. In this embodiment, member channel 410 is shown as but, in no way limited in shape to a fixed diameter channel. As mentioned regarding the previously described embodiment, this portion of surgical guide 200 may be subject to high stress during insertion of tool 2. Tool 2 may also be of such small diameter that added stability is mandated to insure accurate placement. FIG. 2(b) (inset) illustrates a generic tool holder 42. Here, tool holder 42 is a cylinder of length Y with channel 420 appropriately sized to hold tool 2 (not shown) therein. Tool holder 42 is sized to be receivable in member channel 410 so that tool 2 is properly directed toward surgical target T. Length Y may vary depending on the particular surgical location. In the embodiment of FIG. 2(a), length Y may beneficially be somewhat longer than the length of extender section 41 plus the distance between track 331(332) and the point at which tool 2 would enter the body of the surgical subject. The object is to provide sufficient support when pressure and torque are applied along length Y. In FIG. 2(b), tool holder 42 is shown to be tapered (at entry end 421) to, perhaps, provide additional stability, impinging the subject. Other geometries to provide similarly added stability may be utilized. Not presented to be a limiting example, entry end 421 might not be tapered as is shown in the figure but might be serrated or otherwise shaped for stability when impinging the subject.

Figure 3:
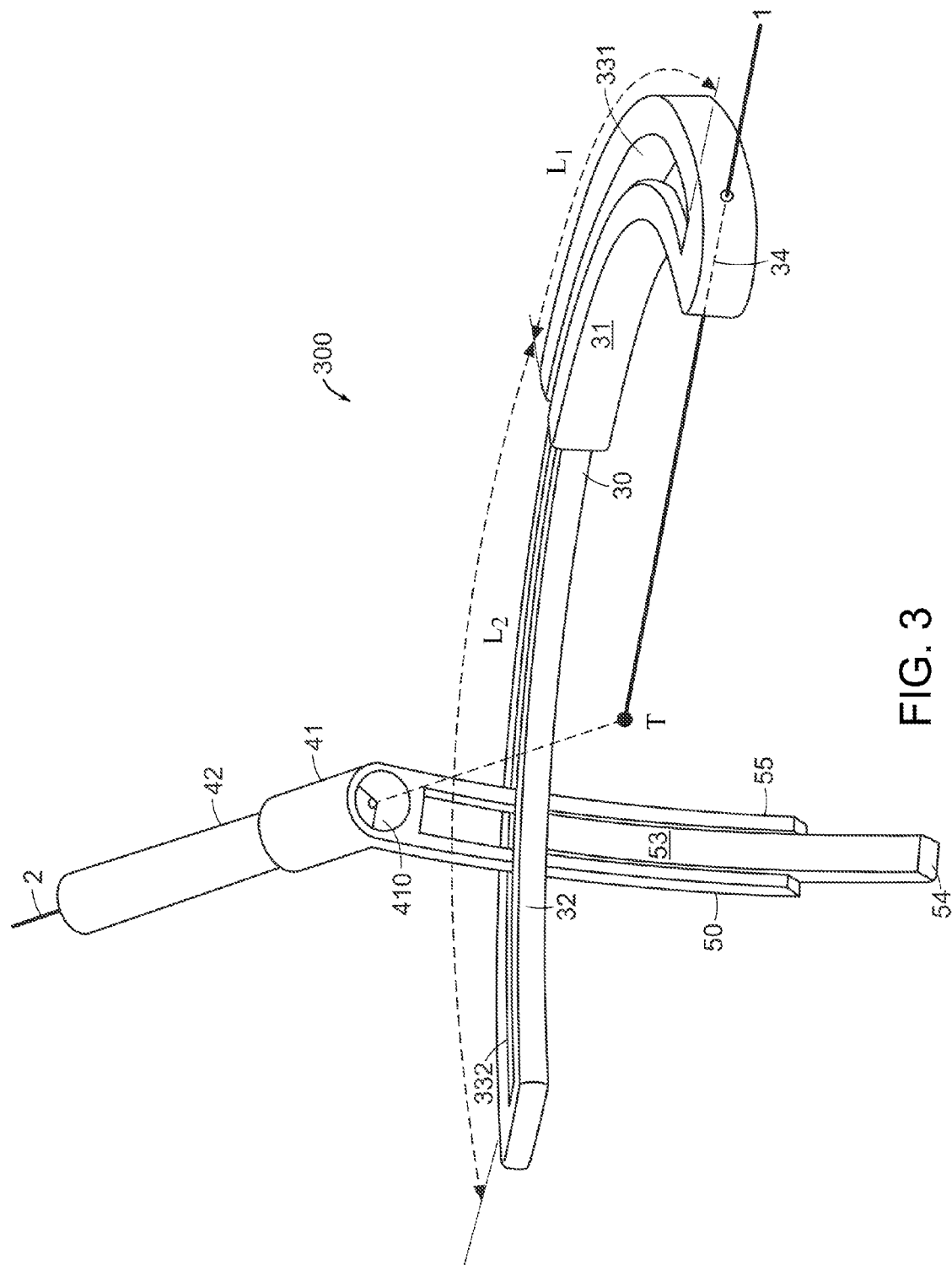
FIG. 3 shows a surgical guide in accordance with another embodiment.

FIG. 3 illustrates another surgical guide 300 embodiment. Base 30 has the same elements as did the base shown in FIG. 2(a). In FIG. 3, most of second base portion 32 is shown to reside outside the base portion orifice of first base portion 31, adding a much larger operator-adjustable effective arc length $L_2$ of track 332 to arc length $L_1$ of track 331. Member 50 is shown to be slidingly engaged through track 332. While the details of tool 2, inserted in tool holder 42, in turn, inserted through member channel 410 are the same for member 50 as in the previously described embodiment (for member 40), member 50 has two portions: slider portion 53 and holder portion 55 by selectively inserting part of slider portion 53 into a member portion orfice of holder portion 55. Slider portion 53 is slidingly engageable with holder portion 55 so that a variable arc length of member 50 may be chosen. To facilitate compact storage of member 50 when the guide 300 is not in use or to facilitate initial engagement of member 50 with base 30 followed by increased operator flexibility in a surgical procedure area of limited space/accessibility, slider portion 53 may beneficially totally reside within holder portion 55 so that the location of edge 54 of slider portion 53 does not extend beyond holder portion 55. As one of skill in the art can readily see, the availability to an operator of variable arc length capability of both track 331(332) and member 50 greatly increases the flexibility in procedural details (in particular in the numerous spatial approaches) without sacrificing tool placement accuracy.

It is to be understood that guide embodiments shown are, with respect to the slidingly engageable components, relying on interference or frictional fits to provide rigidity and stability during operation. If such frictional designs are insufficient in specific circumstances, locking mechanisms known to all skilled in the art are considered to be incorporated for each component having selectable positions.

Figure 4:
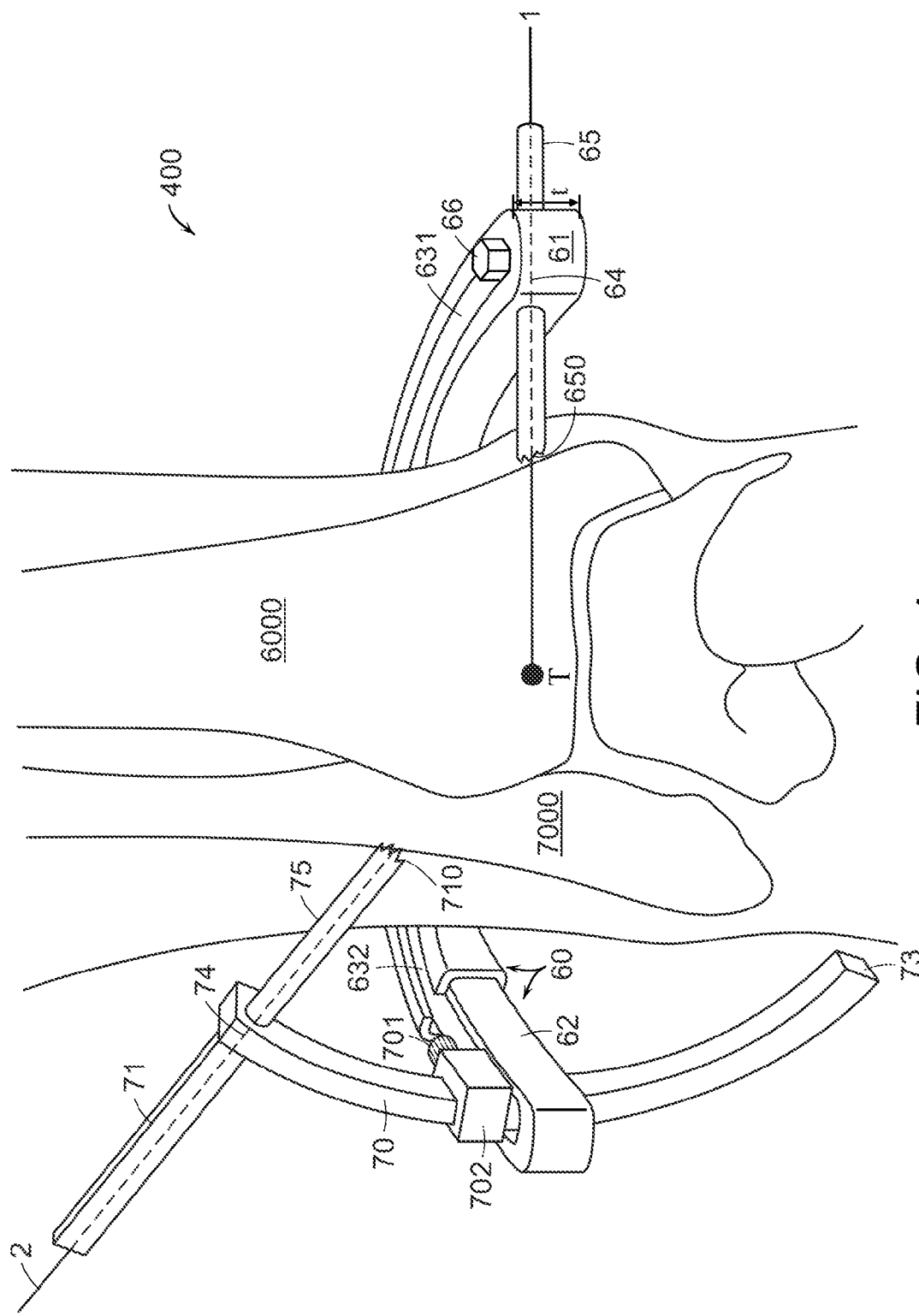
FIG. 4 depicts the use of yet another surgical guide embodiment in ankle surgery.

FIG. 4 illustrates another variation of surgical guide 400 placed in an ankle surgery environment. Surgical guide 400 has base 60 and member 70. Base 60 has first base portion 61 and second base portion 62. First base portion 61 has a base portion orifice extending along its length and has track 631 cut through first base portion thickness t. Track 631 has a uniform track width and also has a constant curvature defining an arc of a base circle. Second base portion 62 has track 632 (having the same uniform track width and constant curvature as track 631) cut through its thickness (which is of somewhat lesser thickness dimension than first base portion thickness t so as to be receivable within the base portion orfice of first base portion 61). As a result, second base portion 62 is slidingly engageable with first base portion 61. Much of second base portion 62 remains within the base portion orifice. A telescopic effect is created so that a variable arc length of base 60 has been chosen by the operator. Second base portion 62 is shown to be held in place (with first base portion 61) only by frictional or interference fit. Base channel 64 is sized to accept locator tool holder 65 through which locator tool 1 passes in the direction of surgical target T located inside tibia 6000. Leading edge 650 of locator tool holder 65 is serrated and makes firm contact with outer cortex of tibia 6000. A serrated edge may provide greater stability to a tool and/or tool holder, and may reduce or prevent damage to soft tissue at a surgical site. Note is then made by the operator as to various distances related to the position of locator tool holder 65 relative to track 631 and starting length of locator tool 1. Set screw (locking mechanism) 66 is tightened to secure the position of locator tool holder 65 and, possibly, of locator tool 1. While guide 400 insures that both locator tool 1 and tool 2 are aimed at surgical target T, the position of holder 65 noted above will, based on the reference sphere created (with center T) determine when insertion of tool 2 will reach target T.

Member 70 is shown having a single element with a defined member arc length. The cross-section of edge 73, as well that of the entire length of member 70 are sized to be acceptable into and to slidingly engage with track 631 (or, equivalently, and in this case track 632) to provide both height and angular variation to the entry of tool 2 as tool 2 is to be directed toward surgical target T along a radius of the reference sphere. In this embodiment, once the desired height and angular position are determined, member 70 is held by set screw 701 to member stop 702. Member stop 702 is sized so as to rest upon and not pass through track 632. Member 70 also has extender section 71. Member 70 has member channel 74 disposed within it. In this embodiment, member channel 74 is shown as but, in no way limited in shape to a fixed diameter channel sized to accept tool holder 75. As mentioned regarding the previously described embodiment, this portion of surgical guide 400 may be subject to high stress during insertion of tool 2. Tool 2 may also be of such small diameter that added stability is mandated to insure accurate placement. In this embodiment, tool 2 is shown inserted into extender section 71 and directed toward surgical target T through tool holder 75. Leading edge 710 of tool holder 75 is serrated and makes firm contact with outer cortex of fibula 7000. A comparison of the distances between member 70 proximate to member channel 74 and the initial lengths of locator tool 1 and tool 2 indicates to the operator when, upon forcing or drilling tool 2 in the direction, the leading edge of tool 2 will reach surgical target T.

Figure 5:
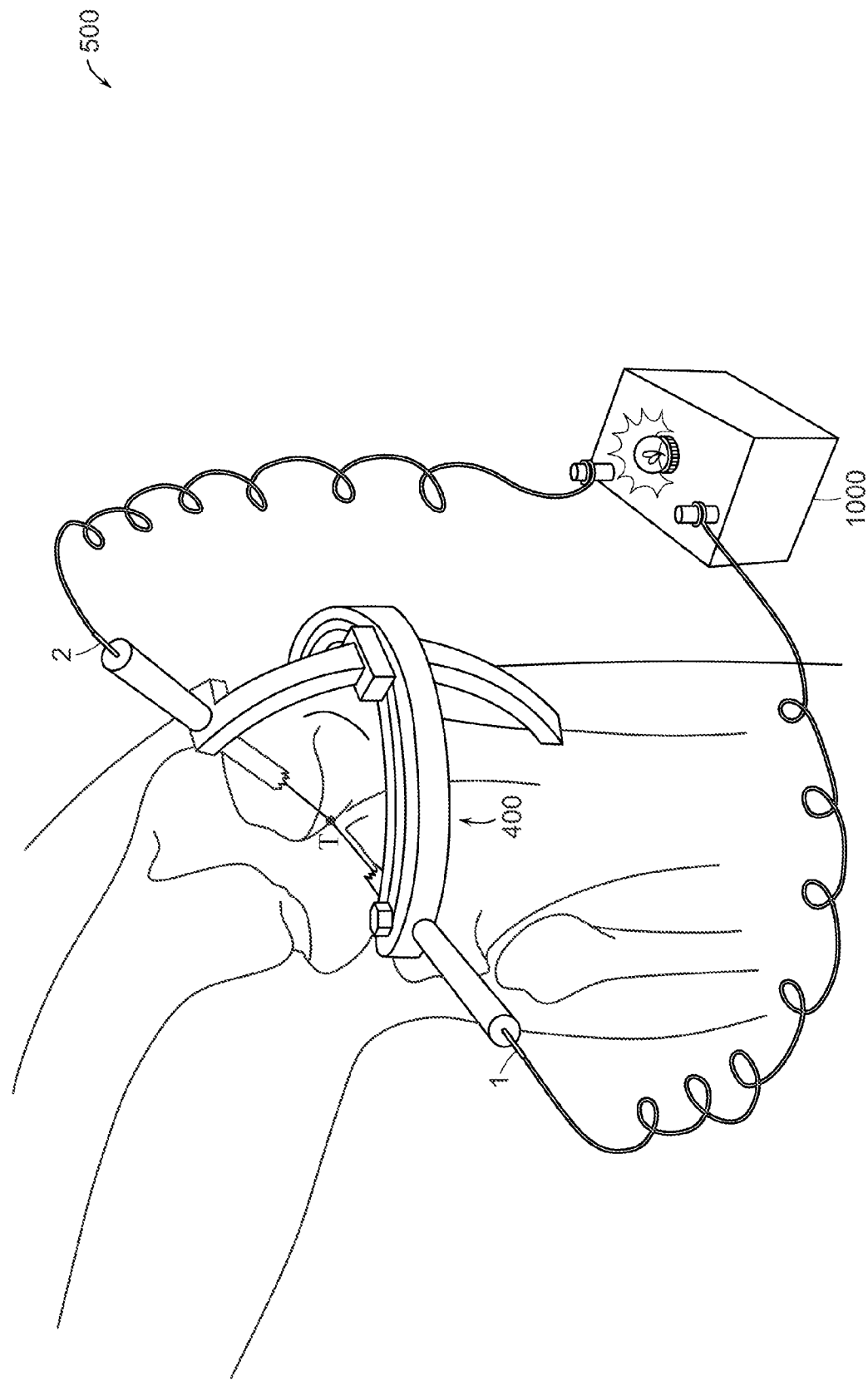
FIG. 5 illustrates a surgical guide kit embodiment used in knee surgery.

FIG. 5 illustrates an embodiment of a surgical guide kit 500. Assuming that locator tool 1 and tool 2 are significantly more electrically conductive than the other elements of surgical guide 400 and the contacted anatomical parts, putting the trailing ends of these tools into an electrical circuit will, when their leading ends couple at surgical target T, complete the circuit. Light or other sensor 1000 would then be activated. This would then complete the surgeon's task without resorting to expensive and potentially detrimental imaging techniques.

Figure 6:
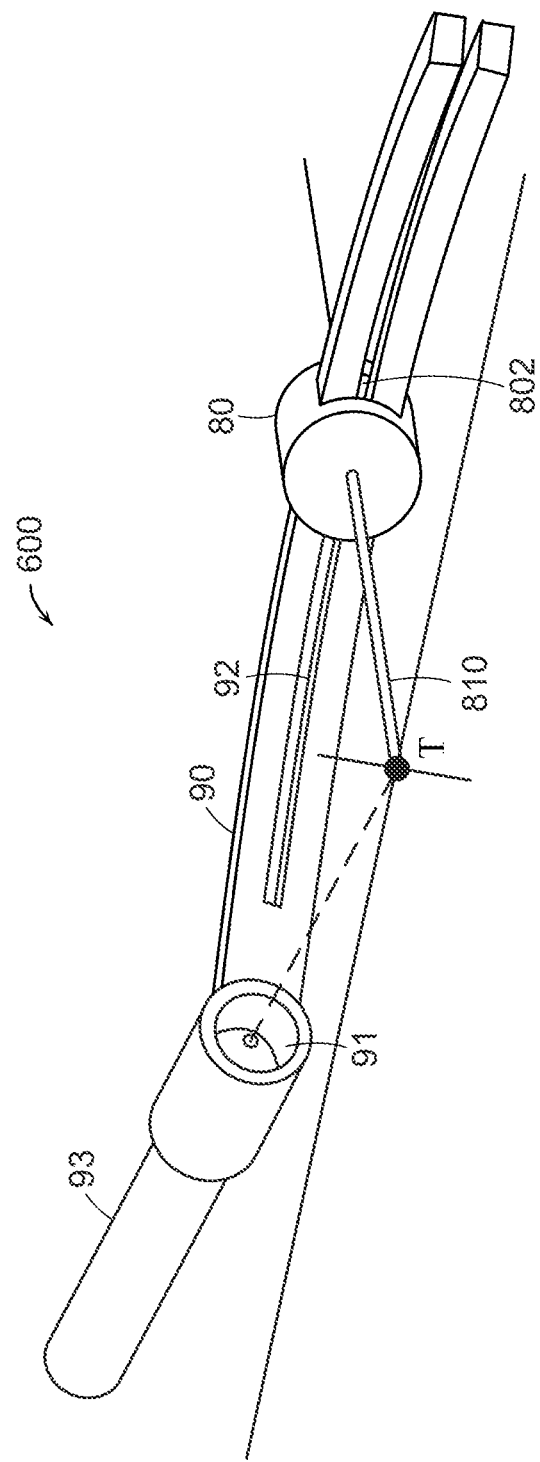
FIG. 6 depicts a surgical guide in accordance with a further embodiment.

FIG. 6 illustrates another surgical guide 600 embodiment for aiming a tool (not shown) toward a surgical target T. Base 80 has the same elements as did the base shown in FIG. 1(*b*). In FIG. 6, the base 80 has a reduced base arc length. Member 90 is shown to be slidingly engaged with base 80 through track 802, as in previous embodiments. Member 90 includes track 92 so as to prevent obstruction by locator tool 810 while operator is selectively orienting member 90 within base 80. The details of tool holder 93, inserted through member channel 91 are the same for member 90 as in previously described embodiments (FIG. 3 tool holder 42 and member channel 410 in member 50). As one of skill in the art can readily see, the reduced size of base 80 may be suitable for surgical procedures performed on smaller anatomical regions (hand and/or foot) or when the at least one tool need not be significantly offset from the locator tool 810 within the plane of base 80.

It is to be understood that any and all of the surgical guide embodiments may include more than one member element to be used simultaneously during a procedure. In particular, utilization of locking mechanisms for these member elements facilitates sequential or serial placements. Alternatively, member elements may be designed to be removable without removing the entire guide from the procedural area.

Although the invention has been described with reference to several embodiments, it will be understood by one of ordinary skill in the art that various modifications can be made and extension to other types of surgical guides can be made without departing from the spirit and the scope of the invention, as set forth in the claims.

What is claimed is:

1. A surgical guide for aiming at least one tool toward a surgical target, the guide having a guide reference plane, the surgical guide comprising:
   a base having a base thickness, a base width disposed within the reference plane, a track cut through the base thickness, the track having a uniform track width, the track having a constant track curvature so as to define a base arc of a base circle, the base circle oriented within the reference plane, the base having a base channel cut through the base width, the base channel disposed within the reference plane, the base channel sized and shaped so as to be capable of accepting a locator tool therethrough; and
   at least one member sized so as to be receivable in the track to engage with the base, the at least one member having a constant member curvature equal to the constant track curvature so as to define a member arc of a member circle, so that, when engaged with the base, the member arc is disposed within a member arc plane that is oriented orthogonal to the reference plane, the base circle and the member circle defining a sphere having a sphere center located at the surgical target, the at least one member having a member channel cut through the member, the member channel disposed within the member arc plane, the member channel sized and shaped so as to be capable of accepting the at least one tool therethrough,
   such that when the at least one member is engaged with the base, both the base channel and the member channel are aligned toward the surgical target.

2. The surgical guide of claim 1, the base having an adjustable base arc length, the base comprising:
   a first base portion having a first base arc length and having a base portion orifice extending along the first base arc length; and
   a second base portion; the second base portion sized to be insertable into the base portion orifice to slidingly engage with the first base portion, the second base portion having a second base arc length,
   such that when the first and second base portions are engaged, the adjustable base arc length is measurable by adding the first base arc length to an adjustable fraction of the second base arc length.

3. The surgical guide of claim 2 further comprising:
   a base locking mechanism to rigidly secure the first and second base portions together at a chosen adjustable base arc length.

4. A method for rigidly securing an adjustable base arc length of the surgical guide of claim 3, the method comprising:
   sliding the second base portion within the first base portion to a chosen base arc length; and
   engaging the base locking mechanism.

5. A method for adjusting the base arc length of the surgical guide of claim 2, the method comprising:
   sliding the second base portion within the first base portion to a chosen base arc length.

6. The surgical guide of claim 1, the at least one member further comprising:
   a channeled tool support member extender section, a channel of the extender section aligned with the member channel, the member extender section having an extender section length slidingly adjustable along a radius of the member circle.

7. The surgical guide of claim 1, the base further comprising:
   a channeled tool support base extender section, a channel of the extender section aligned with the base channel, the base extender section slidingly adjustable along a radius of the base circle.

8. A method for aiming at least one tool toward a surgical target, the method comprising:
   defining a surgical target as a position of a proximal end of a locator tool, the locator tool also having a distal end;
   providing the surgical guide of claim 1;
   engaging the base of the surgical guide with the locator tool by passing the distal end of the locator tool through the base channel;
   engaging the at least one member of the surgical guide with the base of the surgical guide; and
   passing the at least one tool through the member channel.

9. A surgical guide kit, the kit comprising:
   the surgical guide of claim 1; and
   an electrical circuit capable of being coupled with the locator tool at one terminus and capable of being coupled with the at least one tool at a second terminus.

10. The surgical guide kit of claim 9 further comprising:
a sensor in electrical communication with the electrical circuit; the sensor activatable only upon completion of the electrical circuit.

11. A surgical guide for aiming at least one tool toward a surgical target, the guide having a guide reference plane, the surgical guide comprising:
a base having a base thickness, the base having a track cut through the base thickness, the track having a constant track curvature so as to define a base arc of a base circle, the base circle spatially oriented in the guide reference plane, the base having a base channel, the base channel sized and shaped so as to be capable of accepting a locator tool therethrough, the base channel oriented upon a radius of the base circle; and
at least one member, the at least one member having a constant member curvature equal to the constant track curvature so as to define a member arc of a member circle, the at least one member having a member channel, the member channel sized and shaped so as to be capable of accepting the at least one tool therethrough, the at least one member sized to be receivable in the track to engage with the base so that, when engaged with the base, the member circle is spatially oriented in a member arc plane, the base circle and the member circle defining a sphere having a sphere center located at the surgical target, the member channel oriented upon a radius of the member circle,
such that when the at least one member is engaged with the base, both the base channel and the member channel are aligned toward the surgical target.

12. The surgical guide of claim 11, the at least one member having an adjustable member arc length, the at least one member comprising:
a first member portion having a first member arc length and having a member portion orifice extending along the first member arc length; and
a second member portion; the second member portion sized to be insertable into the member portion orifice to slidingly engage with the first member portion, the second member portion having a second member arc length,
such that when the first and second member portions are engaged, the adjustable member arc length is measurable by adding the first member arc length to an adjustable fraction of the second member arc length.

13. The surgical guide of claim 12 further comprising:
a member locking mechanism to rigidly secure the first and second member portions together at a chosen adjustable member arc length.

14. A method for rigidly securing an adjustable member arc length of the surgical guide of claim 13, the method comprising:
sliding the second member portion within the first member portion to a chosen member arc length; and
engaging the member locking mechanism.

15. A method for adjusting the at least one member arc length of the surgical guide of claim 12, the method comprising:
sliding the second member portion within the first member portion to a chosen member arc length.

16. A method for selectively orienting the at least one tool within the base of the surgical guide of claim 11, the method comprising:
sliding the at least one member essentially within the guide reference plane and along an arc length of the track disposed within the base of the surgical guide;
sliding the at least one member along an arc length of the member of the surgical guide; and positioning the at least one member within the base of the surgical guide at the selected orientation.

17. The surgical guide of claim 11 wherein the member arc plane is oriented orthogonal to the guide reference plane.

18. The surgical guide of claim 11, the base having an adjustable base arc length, the base comprising:
a first base portion having a first base arc length and having a base portion orifice extending along the first base arc length; and
a second base portion; the second base portion sized to be insertable into the base portion orifice to slidingly engage with the first base portion, the second base portion having a second base arc length,
such that when the first and second base portions are engaged, the adjustable base arc length is measurable by adding the first base arc length to an adjustable fraction of the second base arc length.

19. The surgical guide of claim 18 further comprising:
a base locking mechanism to rigidly secure the first and second base portions together at a chosen adjustable base arc length.

20. The surgical guide of claim 19, the at least one member having an adjustable member arc length, the at least one member comprising:
a first member portion having a first member arc length and having a member portion orifice extending along the first member arc length; and
a second member portion; the second member portion sized to be insertable into the member portion orifice to slidingly engage with the first member portion, the second member portion having a second member arc length,
such that when the first and second member portions are engaged, the adjustable member arc length is measurable by adding the first member arc length to an adjustable fraction of the second member arc length.

21. The surgical guide of claim 20 further comprising:
a member locking mechanism to rigidly secure the first and second member portions together at a chosen adjustable member arc length.

22. The surgical guide of claim 21, the at least one member further comprising:
a channeled tool support member extender section, a channel of the extender section aligned with the member channel, the member extender section having an extender section length slidingly adjustable along a radius of the member circle.

23. The surgical guide of claim 21, the base further comprising:
a channeled tool support base extender section, a channel of the extender section aligned with the base channel, the base extender section slidingly adjustable along a radius of the base circle.

24. A method for aiming at least one tool toward a surgical target, the method comprising: defining a surgical target as a position of a proximal end of a locator tool, the locator tool also having a distal end; providing the surgical guide of claim 20; engaging the base of the surgical guide with the locator tool by passing the distal end of the locator tool through the base channel; engaging the at least one member of the surgical guide with the base of the surgical guide; and passing the at least one tool through the member channel.

25. A method for rigidly securing an adjustable base arc length of the surgical guide of claim 19, the method comprising:

sliding the second base portion within the first base portion to a chosen base arc length; and
engaging the base locking mechanism.

26. A method for adjusting the base arc length of the surgical guide of claim 18, the method comprising:
sliding the second base portion within the first base portion to a chosen base arc length.

27. The surgical guide of claim 11, the at least one member further comprising:
a channeled tool support member extender section, a channel of the extender section aligned with the member channel, the member extender section having an extender section length slidingly adjustable along a radius of the member circle.

28. The surgical guide of claim 11, the base further comprising:
a channeled tool support base extender section, a channel of the extender section aligned with the base channel, the base extender section slidingly adjustable along a radius of the base circle.

29. A surgical guide kit, the kit comprising:
the surgical guide of claim 11; and
an electrical circuit capable of being coupled with the locator tool at one terminus and capable of being coupled with the at least one tool at a second terminus.

30. The surgical guide kit of claim 29 further comprising:
a sensor in electrical communication with the electrical circuit; the sensor activatable only upon completion of the electrical circuit.

31. A surgical guide kit, the kit comprising:
the surgical guide of claim 11;
the locator tool;
the at least one tool; and
an electrical circuit capable of being coupled with the locator tool at one terminus and capable of being coupled with the at least one tool at a second terminus.

32. A method for aiming at least one tool toward a surgical target, the method comprising: defining a surgical target as a position of a proximal end of a locator tool, the locator tool also having a distal end;
providing the surgical guide of claim 11; engaging the base of the surgical guide with the locator tool by passing the distal end of the locator tool through the base channel; engaging the at least one member of the surgical guide with the base of the surgical guide; and passing the at least one tool through the member channel.

33. A surgical guide for aiming at least one tool toward a surgical target, the guide having a guide reference plane, the surgical guide comprising:
a base having a base thickness, a base width disposed within the reference plane, a track cut through the base thickness, the track having a uniform track width, the track having a constant track curvature so as to define a base arc of a base circle, the base circle oriented within the reference plane, the base having a base channel cut through the base width, the base channel disposed within the reference plane, the base channel sized and shaped so as to be capable of accepting a locator tool therethrough, the base having an adjustable base arc length, the base having a first base portion having a first base arc length and having a base portion orifice extending along the first base arc length and a second base portion; the second base portion sized to be insertable into the base portion orifice to slidingly engage with the first base portion, the second base portion having a second base arc length, such that when the first and second base portions are engaged, the adjustable base arc length is measurable by adding the first base arc length to an adjustable fraction of the second base arc length; and
at least one member sized so as to be receivable in the track to engage with the base, the at least one member having a constant member curvature equal to the constant track curvature so as to define a member arc of a member circle, so that, when engaged with the base, the member arc is disposed within a member arc plane that is oriented orthogonal to the reference plane, the base circle and the member circle defining a sphere having a sphere center located at the surgical target, the at least one member having a member channel cut through the member, the member channel disposed within the member arc plane the member channel sized and shaped so as to be capable of accepting the at least one tool therethrough, such that when the at least one member is engaged with the base, both the base channel and the member channel are aligned toward the surgical target.

34. The surgical guide of claim 33 further comprising:
a base locking mechanism to rigidly secure the first and second base portions together at a chosen adjustable base arc length.

35. A method for adjusting the base arc length of the surgical guide of claim 33, the method comprising:
sliding the second base portion within the first base portion to a chosen base arc length.

36. A surgical guide for aiming at least one tool toward a surgical target, the guide having a guide reference plane, the surgical guide comprising:
a base having a base thickness, the base having a track cut through the base thickness, the track having a constant track curvature so as to define a base arc of a base circle, the base circle spatially oriented in the guide reference plane, the base having a base channel, the base channel sized and shaped so as to be capable of accepting a locator tool therethrough, the base channel oriented upon a radius of the base circle, the base having an adjustable base arc length, the base having a first base portion having a first base arc length and having a base portion orifice extending along the first base arc length and a second base portion; the second base portion sized to be insertable into the base portion orifice to slidingly engage with the first base portion, the second base portion having a second base arc length, such that when the first and second base portions are engaged, the adjustable base arc length is measurable by adding the first base arc length to an adjustable fraction of the second base arc length; and
at least one member, the at least one member having a constant member curvature equal to the constant track curvature so as to define a member arc of a member circle, the at least one member having a member channel, the member channel sized and shaped so as to be capable of accepting the at least one tool therethrough, the at least one member sized to be receivable in the track to engage with the base so that, when engaged with the base, the member circle is spatially oriented in a member arc plane, the base circle and the member circle defining a sphere having a sphere center located at the surgical target, the member channel oriented upon a radius of the member circle,
such that when the at least one member is engaged with the base, both the base channel and the member channel are aligned toward the surgical target.

37. The surgical guide of claim 36 further comprising:
a base locking mechanism to rigidly secure the first and second base portions together at a chosen adjustable base arc length.

38. A method for rigidly securing an adjustable base arc length of the surgical guide of claim 37, the method comprising:
sliding the second base portion within the first base portion to a chosen base arc length; and
engaging the base locking mechanism.

39. A method for adjusting the base arc length of the surgical guide of claim 36, the method comprising:
sliding the second base portion within the first base portion to a chosen base arc length.

40. The surgical guide of claim 36, the at least one member having an adjustable member arc length, the at least one member comprising:
a first member portion having a first member arc length and having a member portion orifice extending along the first member arc length; and
a second member portion; the second member portion sized to be insertable into the member portion orifice to slidingly engage with the first member portion, the second member portion having a second member arc length,
such that when the first and second member portions are engaged, the adjustable member arc length is measurable by adding the first member arc length to an adjustable fraction of the second member arc length.

* * * * *

UNITED STATES PATENT AND TRADEMARK OFFICE
CERTIFICATE OF CORRECTION

| | | |
|---|---|---|
| PATENT NO. | : 8,491,599 B2 | Page 1 of 1 |
| APPLICATION NO. | : 12/641342 | |
| DATED | : July 23, 2013 | |
| INVENTOR(S) | : Heilala et al. | |

It is certified that error appears in the above-identified patent and that said Letters Patent is hereby corrected as shown below:

In the Specifications:

Beginning on column 5, line 56, the text should read:

"portion 55. Slider portion 53 is slidingly engageable with holder portion 55 by selectively inserting part of slider portion 53 into a member portion orifice of holder portion 55 so that a variable arc length of member 50 may be chosen."

At column 6, line 23, replace "orfice" with "orifice"

Signed and Sealed this
Seventeenth Day of September, 2013

Teresa Stanek Rea
*Deputy Director of the United States Patent and TrademarkOffice*